United States Patent
Clements

(10) Patent No.: US 11,426,543 B2
(45) Date of Patent: *Aug. 30, 2022

(54) DRY POWDER INHALER AND FLEXIBLE BAG SPACER DEVICE FOR A DRY POWDER INHALER

(71) Applicant: Inspiring Pty Ltd, Dalkeith (AU)

(72) Inventor: Barry Spencer Clements, Dalkeith (AU)

(73) Assignee: Inspiring Pty Ltd, Dalkeith (AU)

( * ) Notice: Subject to any disclaimer, the term of this patent is extended or adjusted under 35 U.S.C. 154(b) by 342 days.

This patent is subject to a terminal disclaimer.

(21) Appl. No.: 16/606,091

(22) PCT Filed: Apr. 18, 2018

(86) PCT No.: PCT/AU2018/050344
§ 371 (c)(1),
(2) Date: Oct. 17, 2019

(87) PCT Pub. No.: WO2018/191776
PCT Pub. Date: Oct. 25, 2018

(65) Prior Publication Data
US 2021/0001064 A1    Jan. 7, 2021

(30) Foreign Application Priority Data
Apr. 18, 2017  (AU) .............................. 2017901413

(51) Int. Cl.
A61M 15/00  (2006.01)
(52) U.S. Cl.
CPC ...... *A61M 15/0086* (2013.01); *A61M 15/009* (2013.01); *A61M 15/0021* (2014.02);
(Continued)

(58) Field of Classification Search
CPC .......... A61M 15/0021; A61M 15/0086; A61M 15/0088; A61M 15/009; A61M 2205/0216; A61M 2205/0233
See application file for complete search history.

(56) References Cited

U.S. PATENT DOCUMENTS 3,923,043 A * 12/1975 Yanda .................... A61B 5/091
600/541
4,119,097 A * 10/1978 Spector .................... A62B 7/02
128/205.17
(Continued)

FOREIGN PATENT DOCUMENTS

WO    WO-2006/090149 A2    8/2006
WO    WO-2017/181228 A1    10/2017

OTHER PUBLICATIONS

International Search Report; prepared for application No. PCT/AU2018/050344; authorized officer Vivian Cheung; dated Jun. 29, 2018; 6 pages.

*Primary Examiner* — Kathryn E Ditmer
(74) *Attorney, Agent, or Firm* — Winstead PC

(57) ABSTRACT

Provided is a Dry Powder Inhaler (DPI) arrangement comprising a DPI arranged in fluid communication with a spacer device (110) comprising a bag (112) and a body (118) including inlet (114) and opposed outlet (116), the inlet (114) and opposed outlet (116) being provided on, and integral with, the body (118). The body (118) and bag (112) combine to form chamber (120) for operatively receiving vaporised dry powder medication. The inlet (114) and outlet (116) each are in the form of a port that is in fluid flow communication with the chamber (120). The inlet (114) and outlet (116) define, and are separated by, a broad V-formation formed as part of the body (118). The body (118) further includes an elliptical lower perimeter (118.1) defining flange (118.2), for demountably receiving bag (112).

16 Claims, 11 Drawing Sheets

(52) U.S. Cl.
CPC ... *A61M 15/0035* (2014.02); *A61M 2202/064* (2013.01); *A61M 2205/0216* (2013.01); *A61M 2205/0233* (2013.01); *A61M 2205/59* (2013.01)

(56) References Cited

U.S. PATENT DOCUMENTS

| | | | | |
|---|---|---|---|---|
| 5,318,016 | A | 6/1994 | Mecikalski | |
| 5,613,489 | A * | 3/1997 | Miller | A61M 15/0086 128/200.14 |
| 5,842,467 | A * | 12/1998 | Greco | A61M 16/0078 128/200.23 |
| 6,158,428 | A * | 12/2000 | Mecikalski | A61M 15/0086 128/200.23 |
| 6,390,090 | B1 | 5/2002 | Piper | |
| 6,401,710 | B1 * | 6/2002 | Scheuch | A61M 15/0086 128/200.21 |
| 6,463,929 | B1 * | 10/2002 | Scheuch | A61M 15/0086 128/200.22 |
| 7,726,310 | B2 * | 6/2010 | Andrus | A61M 15/0088 128/205.13 |
| 9,108,011 | B2 * | 8/2015 | Wachtel | A61M 15/0086 |
| 2002/0069870 | A1 * | 6/2002 | Farmer | A61M 16/0833 128/200.22 |
| 2003/0041859 | A1 * | 3/2003 | Abrams | A61M 15/0086 128/200.22 |
| 2005/0217667 | A1 * | 10/2005 | Dhuper | A61M 15/0086 128/200.23 |
| 2006/0260606 | A1 * | 11/2006 | Coifman | A61M 15/009 128/200.14 |
| 2007/0283954 | A1 * | 12/2007 | Dhuper | A61M 15/0088 128/203.12 |
| 2008/0035143 | A1 * | 2/2008 | Sievers | A61M 11/008 128/203.12 |
| 2008/0210225 | A1 * | 9/2008 | Geiger | A61M 15/0086 128/200.14 |
| 2009/0293873 | A1 * | 12/2009 | Djupesland | A61M 15/0041 128/203.15 |
| 2011/0108025 | A1 * | 5/2011 | Fink | A61M 16/105 128/200.16 |
| 2013/0192597 | A1 * | 8/2013 | McKinnon | A61M 16/0078 128/203.28 |
| 2013/0276781 | A1 * | 10/2013 | Steelman | A61M 15/0023 128/203.12 |
| 2014/0230817 | A1 * | 8/2014 | Richardson | A61M 15/002 128/203.15 |
| 2014/0311483 | A1 | 10/2014 | Engelbreth et al. | |
| 2016/0030687 | A1 * | 2/2016 | Engelbreth | A61M 15/0021 128/200.23 |
| 2016/0256641 | A1 * | 9/2016 | Lisberg | A61M 15/009 |
| 2016/0339187 | A1 * | 11/2016 | Smaldone | A61M 15/0016 |

* cited by examiner

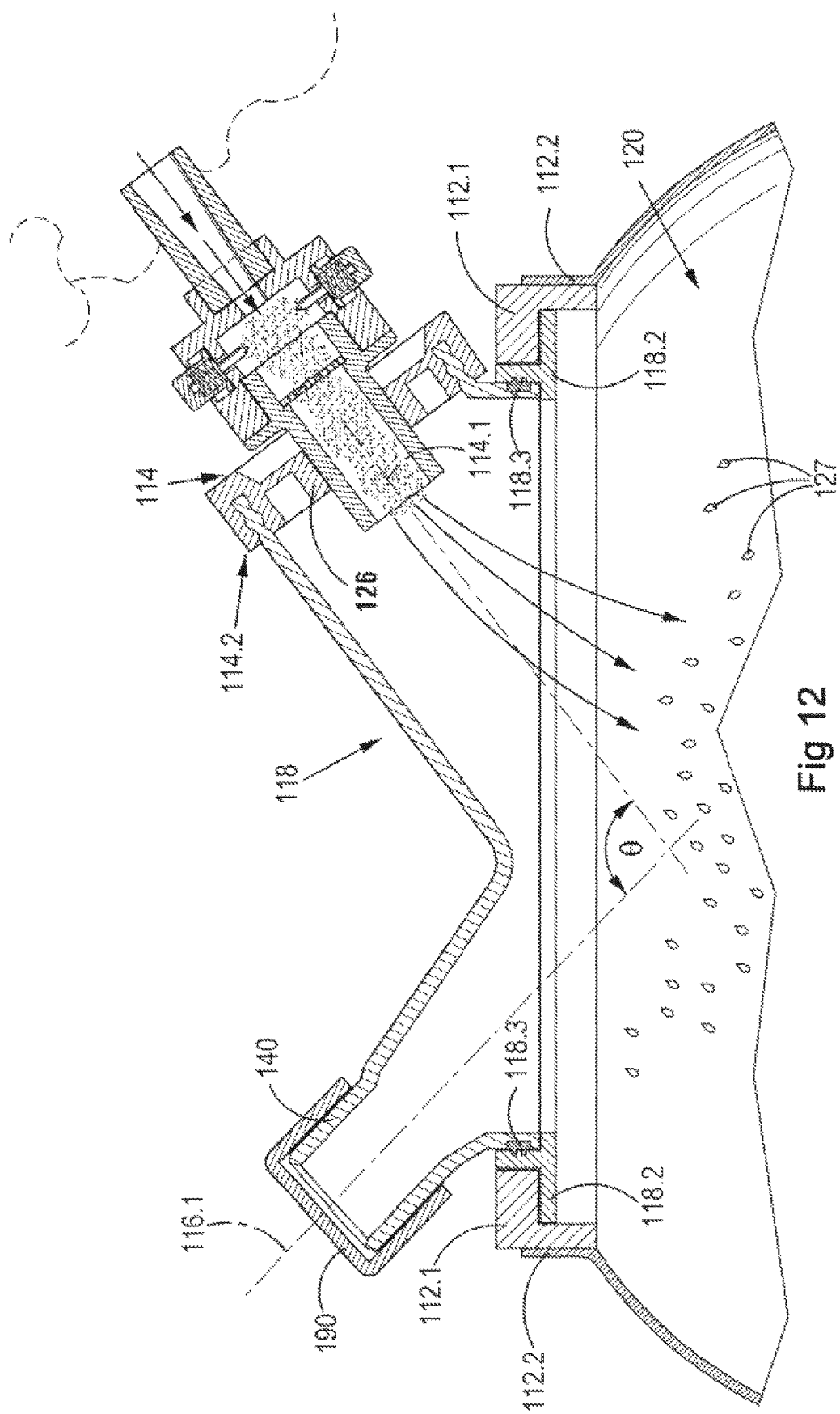

DRY POWDER INHALER AND FLEXIBLE BAG SPACER DEVICE FOR A DRY POWDER INHALER

TECHNICAL FIELD

The present invention relates to a spacer device for an inhaler. More particularly, the present invention relates to a spacer device for use during inhalation of medication from an inhalation drug delivery device, specifically a dry powder inhaler (DPI), as well as to a new dry powder inhaler arrangement.

BACKGROUND ART

The following discussion of the background art is intended to facilitate an understanding of the present invention only. The discussion is not an acknowledgement or admission that any of the material referred to is or was part of the common general knowledge as at the priority date of the application.

Over the past 60 years, inhalation technology has done little to help the average asthmatic or Chronic Obstructive Pulmonary Disease (COPD) sufferer—the largest groups of inhalation device users. This is readily demonstrated by the fact that, in the vast majority of these patients, the amount of inhaled medication reaching the lungs ranges from less than 10% for those patients using a MDI (metered dose inhaler, or "puffer") straight into their mouth, to between 10 and 30% for those using a spacer device, dry powder inhaler, or a standard nebuliser—and this has not improved significantly in all that time. The consequence of this has been huge and expensive drug wastage, poor treatment outcomes, and patient and doctor frustration—all of which has contributed to reduced treatment adherence.

In an effort to address these problems, a report published by the European Respiratory Society and the International Society of Aerosolised Medicine (ERS/ISAM) task force in 2011 highlighted three factors that need to be considered in optimising the chances of inhaled medications reaching their targets in the lung. These three factors are:
 a) Particle size—smaller particles are more likely to reach the airways in greater numbers, penetrate deeper into the lung, spread more evenly through the lung, pass through partially obstructed airways, and reach diseased and damaged areas;
 b) Flow—lower flow rates avoid impaction of particles around corners; and
 c) Breathing pattern—a slow, controlled deep inhalation or, if this cannot be achieved, normal relaxed tidal breathing will improve lung delivery, and airway penetration.

Dry Powder Inhalers (DPIs) or Dry Powder Dispensers (DPDs) are popular as they can be cheap, convenient, easier to use, and can deliver larger doses than MDIs. However, they fail to embrace any of the principles outlined in the ISAM report (see above) to a significant extent. In particular, they require a high flow rate (generally around 30-90 L/min) in order to empty the capsule and de-aggregate the particles. It has been clearly shown that particles travelling at these speeds are more likely to impact and be retained on mucosal surfaces when rounding corners, such as in the pharynx, glottic area and each branch in the airways resulting in only a small number (<30%) reaching the target areas in the lung. All of these factors become even more pertinent in diseased lungs where most drugs will preferentially follow the path of least resistance towards the "healthier" parts of the lung, with very little drug penetrating to areas where it is needed most, such as the peripheral airways, airways clogged with mucus, and damaged areas. In addition, high speed particles impacting on the vocal cords cause cough—by far the commonest complaint from DPI users—often causing them to abandon the device. The high flow rates and breathing techniques required for proper DPI function can also be difficult to attain in sick, elderly, and very young patients. The ISAM report also quotes other studies highlighting that 94% of patients using a DPI do not use it correctly, and 25% of patients have never received technique training for the device.

The current invention was conceived with these shortcomings in mind.

SUMMARY OF THE INVENTION

According to one aspect of the invention, there is provided a spacer device for a Dry Powder Inhaler (DPI), the spacer device comprising:
 a body having an inlet and an outlet opposed from the inlet;
 a demountable, flexible bag attached to the body, the bag and body together defining a chamber, such that the inlet and outlet are in fluid flow communication with an interior of the chamber;
 wherein the inlet is configured for operative connection to the DPI containing a drug to be inhaled;
 wherein the outlet is configured to be operatively received by a user's mouth; and
 wherein the flexible bag serves as reservoir to allow for the formation of a vapour or particle cloud of the drug to be inhaled therewithin following activation of the DPI, the flexible bag being configured to be at least partially inflatable and at least partially deflatable commensurate with breathing and/or rebreathing of said user.

The skilled addressee will appreciate that reference herein to a Dry Powder Inhaler (DPI) includes reference to any device configured to deliver medication to the lungs of the user in the form of a dry powder, either via inhalation from the user, or via expulsion through a suitable expulsion configuration, such as pressurised gas, or the like, to form a Dry Powder Dispenser (DPD). Accordingly, reference herein to DPI will be understood to refer to any such inhalation or expulsion actuated devices, albeit a DPI or DPD.

The spacer device may be valveless, i.e. unvalved.

The body, including the inlet and outlet, may be configured to reduce a static electricity charge. The bag may be configured to reduce a static electricity charge. The body (including inlet and outlet), and/or bag may be treated with an anti-static agent. The body (including inlet and outlet), and/or bag may be made of electrically conductive material. The body, including the inlet and/or outlet, may be made of metal or a metallised compound, such as metallised plastic or a metal-coated plastic. The bag may be made of a metallised film or aluminium foil. The metallised film may be a metallised polymer film The inlet may comprise a mount defining an inlet passage for sealingly engaging with a mouthpiece of an inhalation drug delivery device. The inlet may be configured to sealingly receive a mouthpiece of a DPI device. The inlet may be surrounded by a sealing collar configured to seal against the inhalation drug delivery device. The spacer device, including the inlet and outlet, may be valveless. The outlet may comprise a mouthpiece defining an outlet passage. The outlet passage may provide unimpeded air and drug flow between the chamber and the ambient environment or, during use, the person's mouth.

The body may be external to the bag. The bag may depend operatively downwardly from the body.

The body may be in the form of a generally V-shaped mounting. The V-shaped mounting may be formed by the opposing inlet passage and the outlet passage intersecting at an angle along their respective longitudinal axes where the angle creating the V defines an arc of preferably between 30 and 170 degrees, preferably 60 to 120 degrees, most preferably 90 degrees.

The inlet and outlet passages may be cone-shaped. The perimeter of the inlet may be round, oval, elliptical, or irregular in shape.

The V-shaped mounting may include a V-shaped interior surface, and may have a lower perimeter formed by the merging of the inferior and lateral aspects of the merging inlet and outlet ports that is generally oval in shape. This perimeter may constitute the portion of the mounting that receives the demountable bag. The interior of the V-shaped mounting is shaped and dimensioned to define a cavity that provides a passage for flow of air and/or medication between the inlet and the bag and between the bag and the mouthpiece.

The interior of the V-shaped cavity may be sized and dimensioned to receive the bag, when the bag is folded into the cavity for portability purposes.

The inlet and outlet passages may be of roughly equal proportion in size, length, volume, diameter, or shape. The inlet and outlet may, in another embodiment, not be proportional in size, length, volume, diameter and/or shape.

The ratio of the major and minor axes of the oval perimeter in this embodiment may be between 1.01:1 and 6:1, preferably between 1.2:1 and 2:1, most preferably 1.38.

The outlet may be configured to be received by a user's mouth, either directly, or through a face mask.

The invention extends in a further aspect thereof to a bag for a spacer device of the invention, wherein the bag has an opening including a collar that is shaped and dimensioned to fit securely to the lower perimeter of the body of the spacer device of the invention, thereby to releasably attach the bag to the body of the spacer device. The collar may extend along an upper periphery of the bag opening, and may extend at least partially around the opening of the bag. The bag opening may be biased towards an open, distended position by way of being made of a resiliently flexible material. The bag when ready for use, may spontaneously adopt a shape of an open inflated/distended position. This may occur through shape or material memory. The bag may be provided with a peripherally extending, resiliently flexible seam. The resiliently flexible seam serves to resist vertical collapse of the bag during inhalation and exhalation.

The capacity for the bag to adopt this shape may be engineered to ensure that negligible resistance to the collapse of the bag during inhalation is present. The collar may be made of a resiliently flexible material that urges the collar (and hence bag) against an inner surface of the mounting, in one embodiment. In another embodiment, the collar may be shaped and dimensioned to encircle and attach in a friction-fit—including an O-ring conformation—or snap-fit manner to the lower perimeter of the body. The bag may also be provided with a threaded collar that engages with a complementarily threaded portion of the lower perimeter of the body.

It is to be understood that the spacer device may include bags of many different sizes and shapes, with the choice depending on a number of factors including, but not limited to: the lung volume and inhalation capabilities of the user; the medical needs at the time of use; and the patient preference (which may include merchandising choices) or to minimize awkwardness and conspicuousness when used in social settings.

Broadly, the invention extends in yet another embodiment thereof to a DPI, the DPI including: a body having an inlet and outlet, the inlet and outlet being in fluid flow communication with a chamber defined within the body, the chamber being shaped and dimensioned to receive a powdered inhalant drug.

The inlet may be shaped and dimensioned to receive expulsion means for expelling the powdered drug from the chamber, through the outlet, into the ambient environment or, in one embodiment, into the spacer device of the invention. The dry powder may be provided in the form of a capsule, caplet, gel covering, or other encapsulation means.

As such, the DPI may include piercing means for piercing the capsule, caplet, gel covering, or other encapsulation means to liberate the powder prior to expulsion from the DPI chamber. The piercing means may be in the form of one or more pins that may be actuated by a user to travel into the DPI chamber, thereby piercing the encapsulation means and liberating the dry powder drug into the DPI chamber. The pins may be spring-loaded such that they automatically retract once released by a user. The pins may be opposed, i.e. on opposite sides of the DPI chamber.

The outlet may have a filter associated therewith to prevent lumps or oversized particles from being expelled from the chamber or outlet. The filter may be proximal the DPI chamber or distal thereto (i.e. close to the exit of the outlet).

In one embodiment of the DPI, the expulsion means may be in the form of a propellant canister, an outlet of which is attached in fluid flow communication with the inlet. The propellant canister may be a compression-activated canister such as those found in meter dose inhalers (MDIs) and may serve to expel a metered dose of propellant into the DPI chamber upon activation thereof.

In another embodiment of the DPI, the expulsion means may be in the form of a conduit connected to a positive pressure pump, such as a nebuliser or oxygen supply.

In a still further embodiment of the DPI, the expulsion means may be in the form of an entrainment mouthpiece shaped and dimensioned to allow a user of the device to expel the contents of the chamber through the outlet by exhalation. When use is made of the entrainment mouthpiece, the opposed outlet of the spacer device may need to be closed. For this purpose, this embodiment of the invention includes a removable cap that occludes the outlet of the spacer device. As such, the outlet cap fits snugly over the outlet of the spacer device.

In a yet further embodiment, the expulsion means may comprise any suitable form of air compressor configured to expel the dry powder medication into the chamber, such as a syringe, a compressible bulb, or the like.

In use, a user will attach the DPI of the invention to an inlet of the spacer device, pierce the encapsulation means to liberate the drug powder, and then activate or use the expulsion means to expel the powder from the DPI chamber, through the DPI outlet, through the spacer device inlet, into the spacer device chamber formed by the spacer device body and the bag associated therewith, from where the vaporised or micro-dispersed drug particles can be inhaled with a slow deep inhalation, and/or regular tidal breathing and/or rebreathing.

The skilled addressee will appreciate that, in the manner described, the spacer device in combination with the DPI facilitates the user to inhale a cloud or vapour of well-dispersed dry powder particles generally within the parameters of the ISAM report, as described above.

With one possible embodiment of the DPI, the user will thus pierce the encapsulation means, followed by activating a metered dose inhaler canister containing simply compressed air or gas—the purpose of which is purely to expel the powder into the chamber. In another possible embodiment of the DPI, the user will pierce the encapsulation means and channel air or oxygen through the DPI and into the interior of the spacer device chamber. In a further embodiment, the user will close the outlet of the spacer device, pierce the encapsulation means, and blow into the entrainment mouthpiece provided on the inlet of the DPI to expel the contents of the DPI chamber into the spacer device chamber. In addition, the user may use a suitable air compressor, such as a bulb or a syringe etc. to expel or pump the dry powdered drug into the chamber where it disperses, ready for comfortable and controlled inhalation by the user.

In these embodiments, once the powder has been expelled into the chamber, the medication is ready for inhalation by the user. In the case of the user blowing into the device, the outlet cap will need to be removed prior to inhalation.

BRIEF DESCRIPTION OF THE DRAWINGS

The description will be made with reference to the accompanying drawings in which:

FIG. 12 shows a cross-sectional side view of another embodiment of the DPI, following piercing of a dry powder capsule.

DETAILED DESCRIPTION OF EMBODIMENTS

Figure 1:
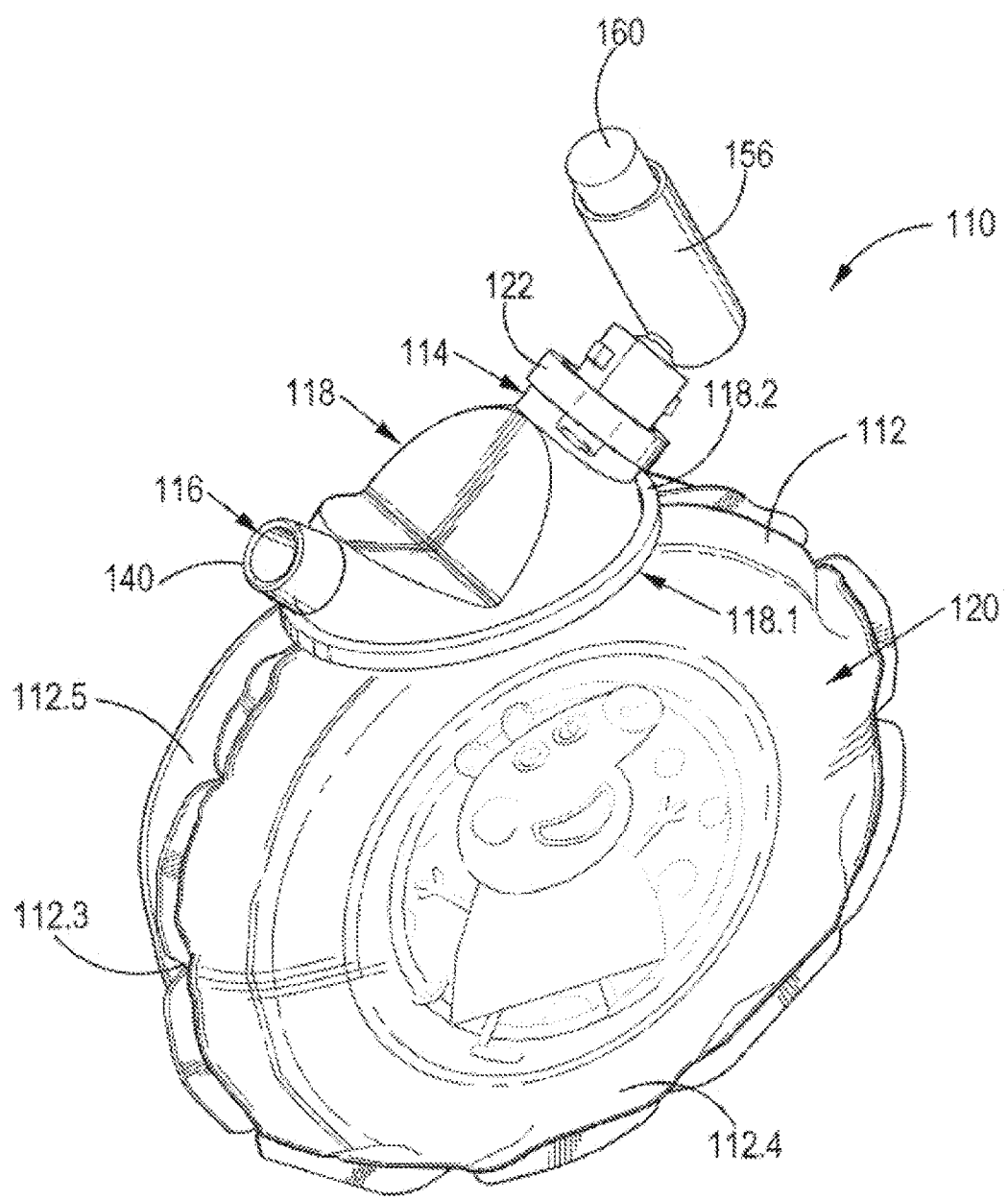
FIG. 1 is a 3-D drawing of a V-shaped spacer device for a DPI and a DPI device in accordance with one aspect of the invention.
Figure 2:
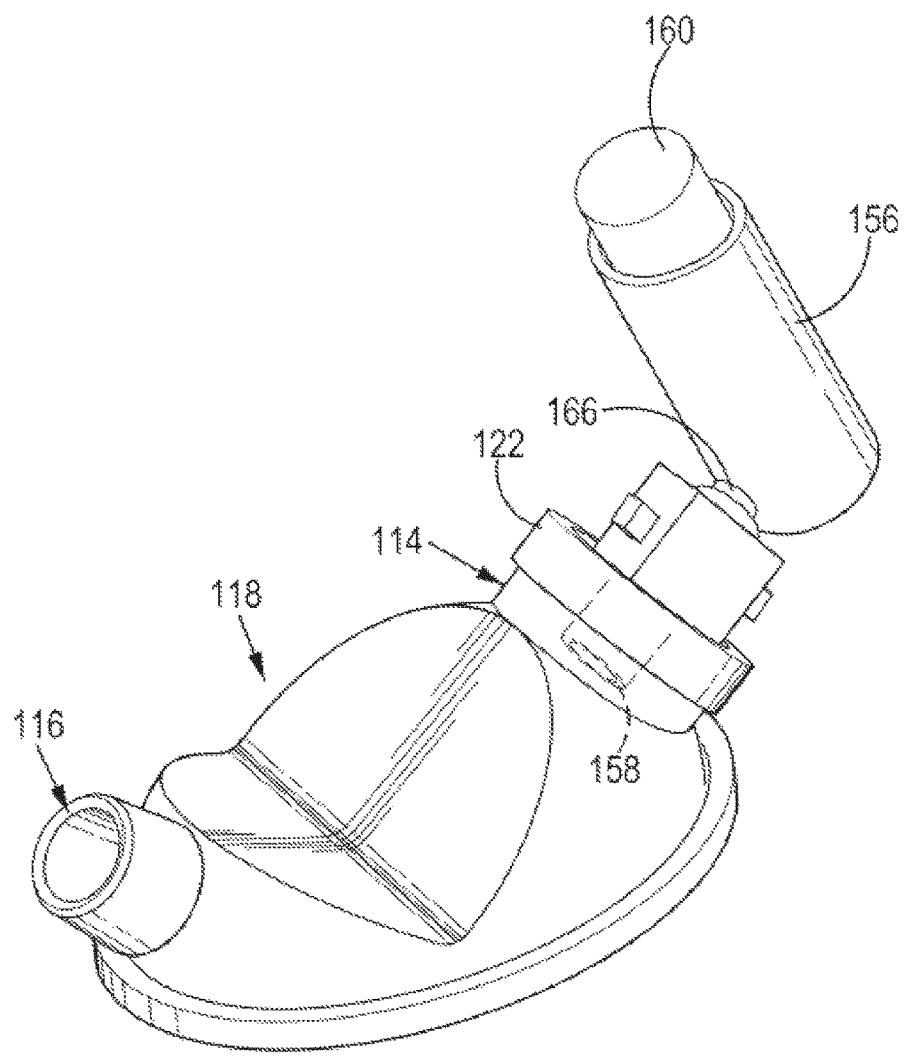
FIG. 2 is a 3-D drawing of the DPI device of FIG. 1, attached to the V-shaped body of the spacer device shown in FIG. 1.

Further features of the present invention are more fully described in the following description of several non-limiting embodiments thereof. This description is included solely for the purposes of exemplifying the present invention to the skilled addressee. It should not be understood as a restriction on the broad summary, disclosure or description of the invention as set out above. In the figures, incorporated to illustrate features of the example embodiment or embodiments, like reference numerals are used to identify like parts throughout.

The invention as described herein relates to a spacer device for facilitating inhalation of dry powdered medication delivered from an inhaler delivery device (such as a DPI). The invention also relates to new embodiments of DPIs. One embodiment is a DPI with a propellant canister in fluid flow connection with an interior of a capsule chamber of the DPI to blow the capsule contents into an interior chamber of the spacer device. A further embodiment is a DPI adapted to receive a conduit with pressurised air into the interior of the capsule chamber. A third embodiment is a DPI with an inlet for allowing a user to pierce the capsule and blow the contents thereof into an interior chamber of the spacer device of the invention.

The current spacer device invention addresses the issues associated with existing devices of which the Applicant is aware by avoiding the need for a rapid coordinated inhalation, and at the same time, allowing the user to inhale the powdered medication slowly, with the minimum of effort and timing required. This in turn results in increased comfort during inhalation and minimises the occurrence of the most common side effect of DPI devices, mainly cough caused by a large concentration of dry powder particles hitting the vocal chords and/or throat at speed, typically in a short time period of less than a second. Of course, this inhalation speed is required to ensure that the dry powder is entrained at a velocity sufficient to exit the DPI and de-aggregate the particles at the same time.

In general, the spacer device of the invention, indicated by reference numeral 110 throughout the drawings, includes a flexible, collapsible bag shaped 112 and dimensioned to serve as reservoir for receiving a drug to be inhaled in a particle cloud or vapour form, and a body (also referred to herein as a "base") with an inlet, or entrance, through which medication is discharged from a DPI into the bag, and an outlet, or exit, typically forming a mouthpiece through which the contents of the bag can be inhaled with the bag collapsing under the negative pressure created by the inhalation thereby promoting the emptying of all its contents into the mouth of the patient and maximising the delivery of medication to the lungs of even unsophisticated users. The spacer device allows for a full dose of inhalant drug to be received within the bag, from where it can be inhaled slowly (and completely) by an unsophisticated user either by way of regular, tidal breathing, or by a slow deep single inhalation.

The elements of the spacer device are generally designed to minimize impaction of drug particles therein or thereupon, thereby promoting laminar flow into and out of the bag and inlets/outlets. This arrangement greatly facilitates increased drug availability and inhalation, allowing the inhalant drug to progress into the furthest stretches of the user's lungs without having to coordinate the emission of the inhalant drug into the bag with inspiration. Increased levels of drug can be inhaled by a slow deep single breath inhalation or regular tidal breathing rather than the sharp, co-ordinated inspiration that is required with all current dry powder inhalation devices of which the Applicant is aware. Usefully, the size of the bag can be swapped to suit a user's needs—age, physical size, lung capacity, strength of inspiration, social awkwardness—and it has been found that a bag as small as 500 cm$^3$ and as large as 1500 cm$^3$ can achieve similar levels of drug particles being inhaled successfully, depending on the factors named above.

Reference numeral 110 refers generally to a spacer device of the invention. In one embodiment of the invention, shown in FIGS. 1 to 12, the spacer device 110 comprises a metallised bag 112 of low, or no, distensibility attached to a body 118. The bag 112 is made of an electrically conductive material, such as a metal or aluminium foil. In another embodiment, the bag 112 is made of a metallised film or metallised biaxially-oriented polyethylene terephthalate (BoPET) or other similar flexible polymer, typically Mylar®. Alternatively, the bag 112 can be treated with an antistatic agent forming a static dissipative coating or layer on the bag 112. The same applies to the body 118, which can be made from, laminated to, or coated with, an anti-static coating or layer. The body 118 is typically made from a metal such as aluminium (although not restricted to this) or a metallised compound (such as metallised plastic, although not restricted to this), or a metal-coated compound such as a high-density plastics material (although not restricted to this).

The body 118 includes inlet 114 and opposed outlet 116, the inlet 114 and opposed outlet 116 being provided on, and integral with, the body 118. The body 118 and bag 112 combine to form chamber 120 for receiving vaporised or micro-dispersed medication from a dry powder inhaler (DPI).

The inlet 114 and outlet 116 each are in the form of a port that is in fluid flow communication with the chamber 120. The inlet 114 and outlet 116 define, and are separated by, a broad V-formation formed as part of the body 118. The body 118 further includes an elliptical or oval lower perimeter 118.1 defining flange 118.2, for demountably receiving bag 112.

Figure 4:
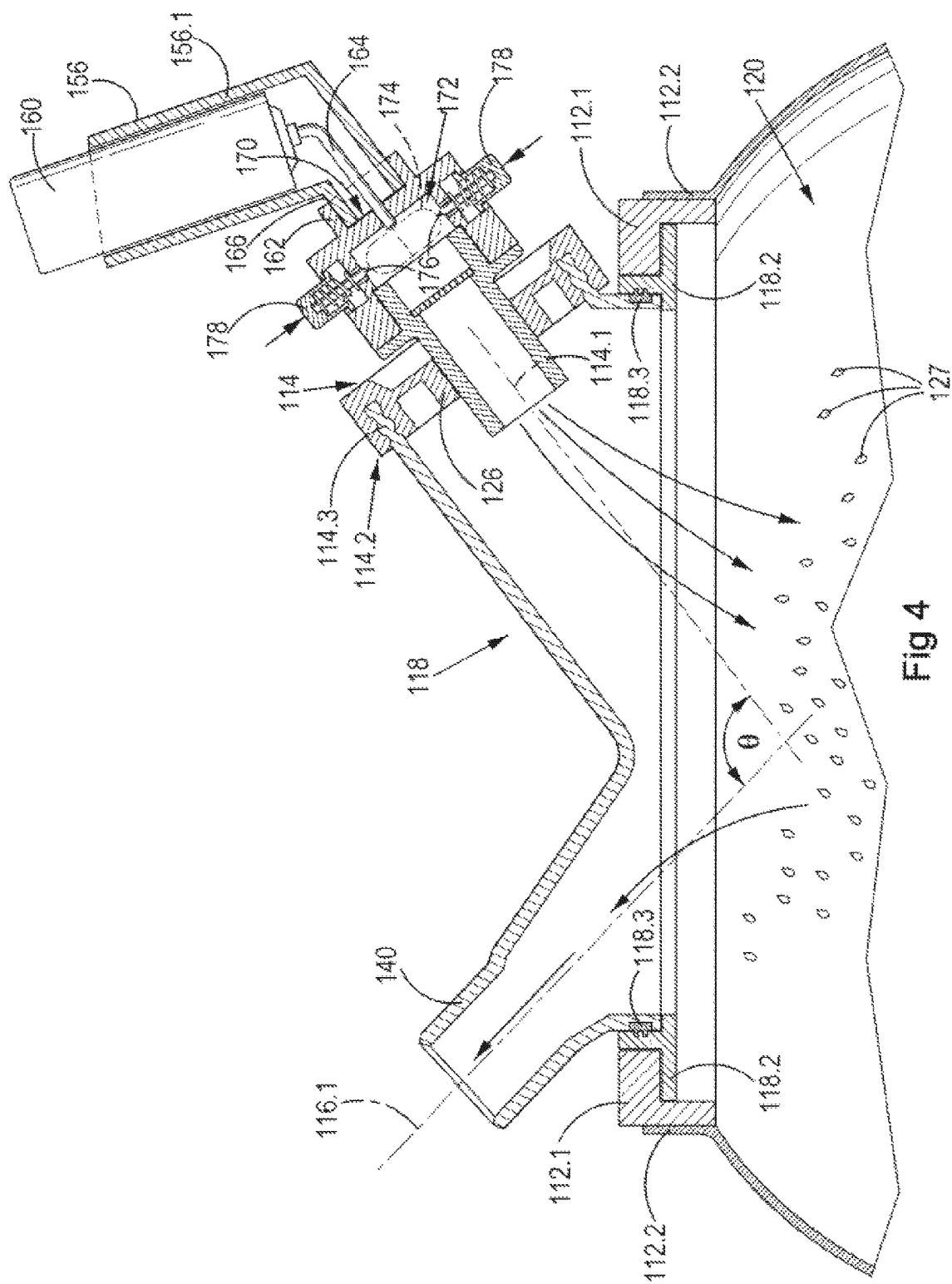
FIG. 4 is a cross-sectional view of the embodiment shown in FIG. 1, showing the flow of dry powder particles expelled from the DPI leading to the formation of a cloud of particles traversing the cavity defined between the body and the bag, as well as showing a cross-sectional view of the DPI of the invention.
Figure 5:
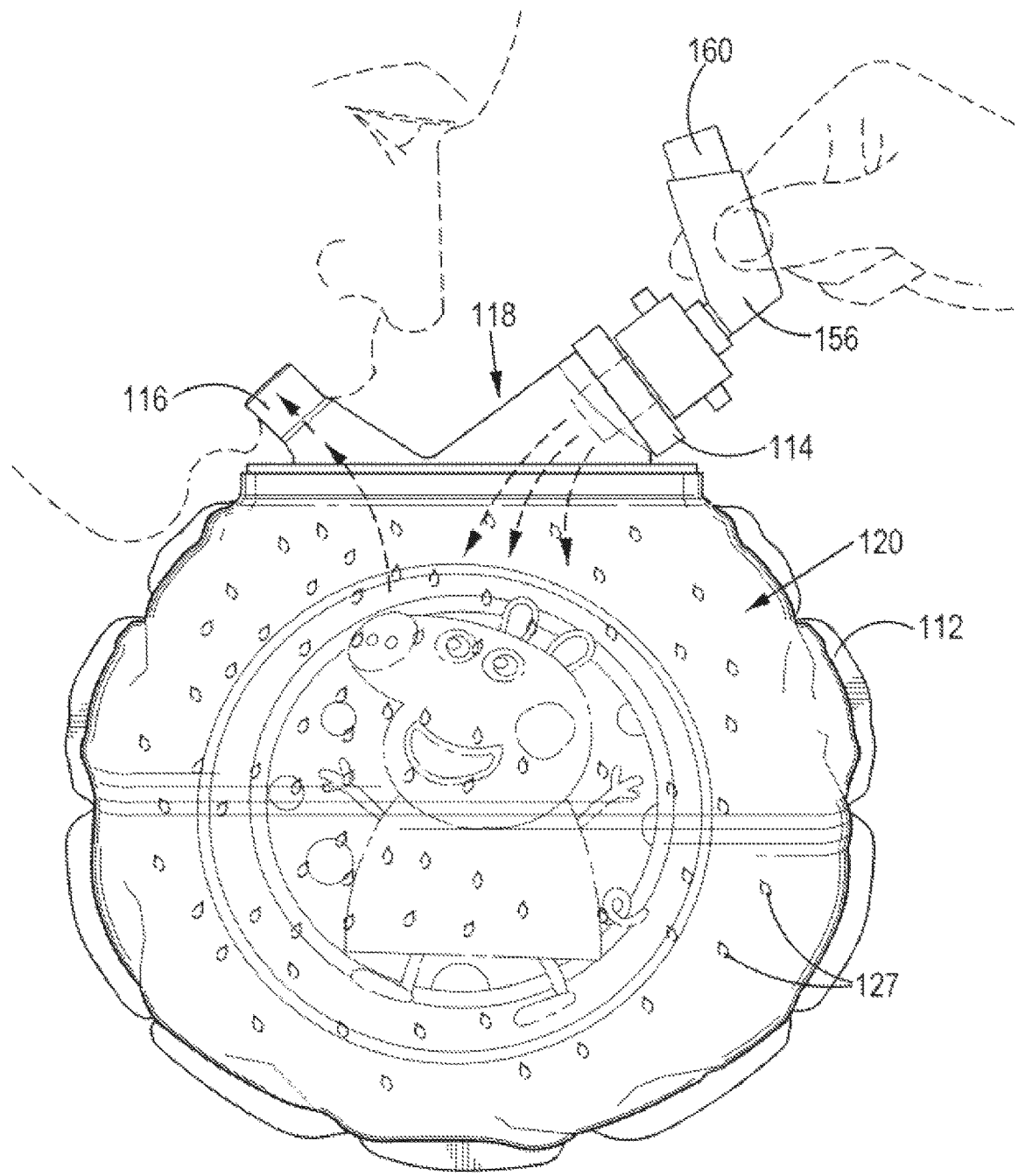
FIG. 5 is a part cross-sectional view of the embodiment of the invention shown in FIG. 1, when in use, showing the cloud of particles now filling the volume of the bag, ready for inhalation.
Figure 9:
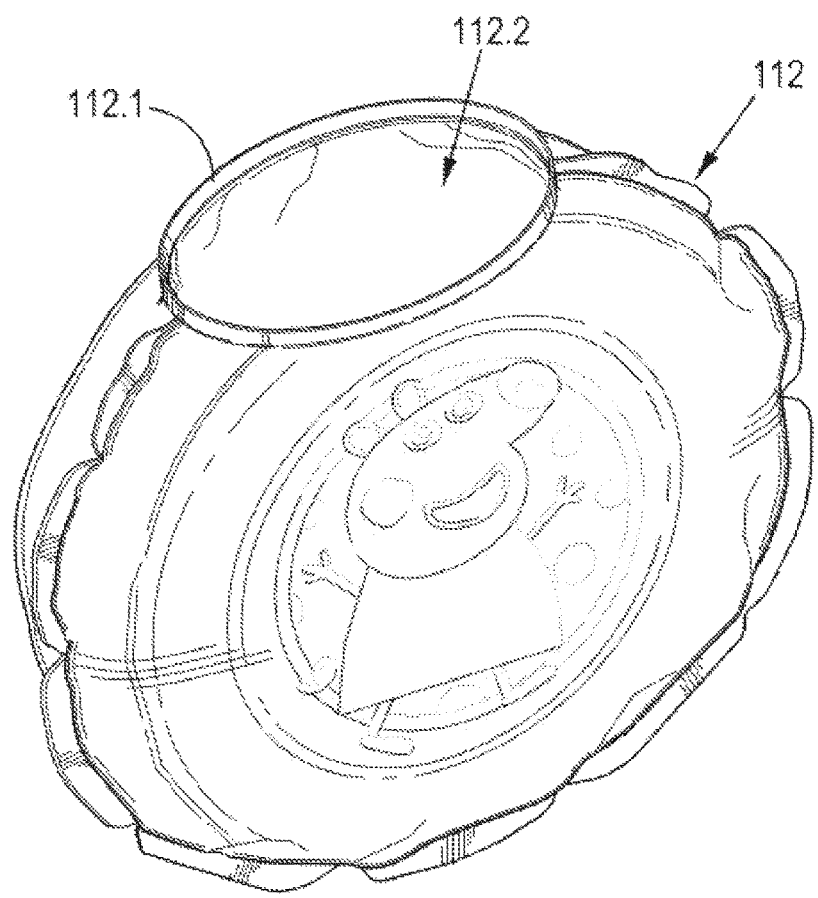
FIG. 9 is a 3-D view of a bag with a collar for attaching to a lower perimeter of the body in accordance with one aspect of the invention, for use with the spacer device shown in FIG. 1.

As may best be seen in FIG. 4, the bag 112 includes a connecting formation in the form of an elasticated, peripherally co-extensive rib 112.1 attached to an opening 112.2 (best seen in FIG. 9) defined within, or attached to, an operatively upper section of the bag 112. The rib 112.1 attaches to the flange 118.2 to provide an effective seal between the bag 112 and the body 118. FIG. 9 also provides an indication of how the bag 112 looks prior to being connected to the perimeter 118.1 of the base/body 118.

In another embodiment (not illustrated), the bag 112 opening 112.2 (and hence rib 112.1) is received over—and thus covers—the flange 118.2, the bag 112 having a constrictive elastic rib or O-ring 112.1 that can provide an effective seal between the bag 112 and the flange 118.2.

The embodiment shown in FIG. 4 shows that the flange 118.2 can be threadedly mounted to the body 118 using thread formations 118.3 to facilitate cleaning or autoclaving of the body 118. In other embodiments the flange 118.2 is formed integrally with the body 118.

Returning to FIG. 1, the inlet 114 includes an annular connector 122 for receiving a mouthpiece 158 of a DPI 156 in fluid flow fashion to the inlet 114, thereby allowing direct communication between the DPI 156 and the chamber 120 to allow for generally unimpeded cloud formation within the chamber 120 when a propellant contained within pressurised canister 160 is released. The annular connector 122 is screwed or clipped on to an end 114.2 of the inlet 114 using threads or interference fittings 114.3 provided proximal to said end 114.2. It is to be understood that the annular connector can also be connected to the inlet 114 in a snap fit or friction fit manner (not shown). The annular connector 122 includes a sealing collar 126 in the form of a resiliently flexible inner annulus for sealingly receiving the mouthpiece 158.

Figure 10:
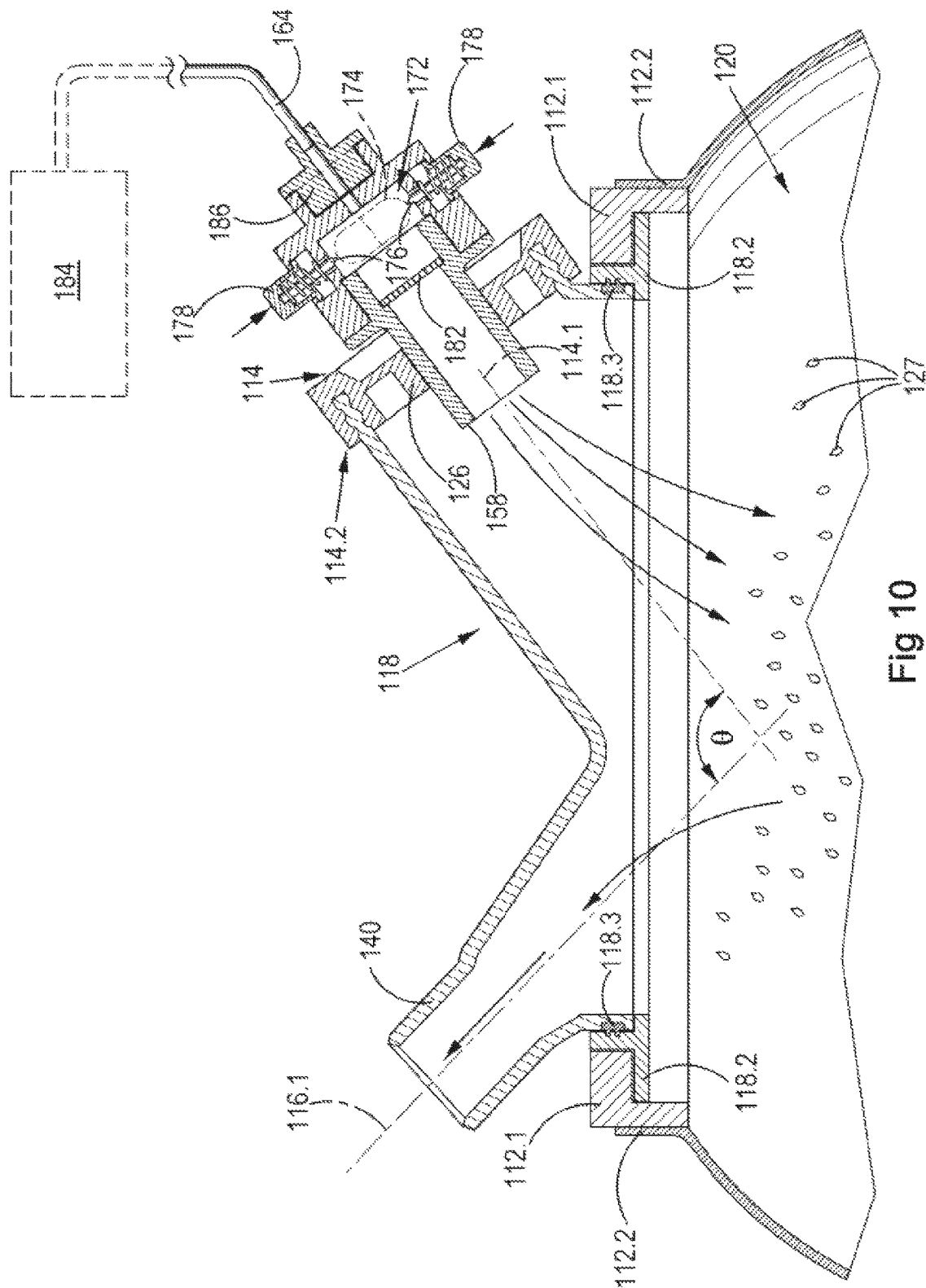
FIG. 10 shows a cross-sectional side view of another embodiment of the DPI, including a conduit from a pressurisation source such as a nebuliser pump, or oxygen source.
Figure 11:
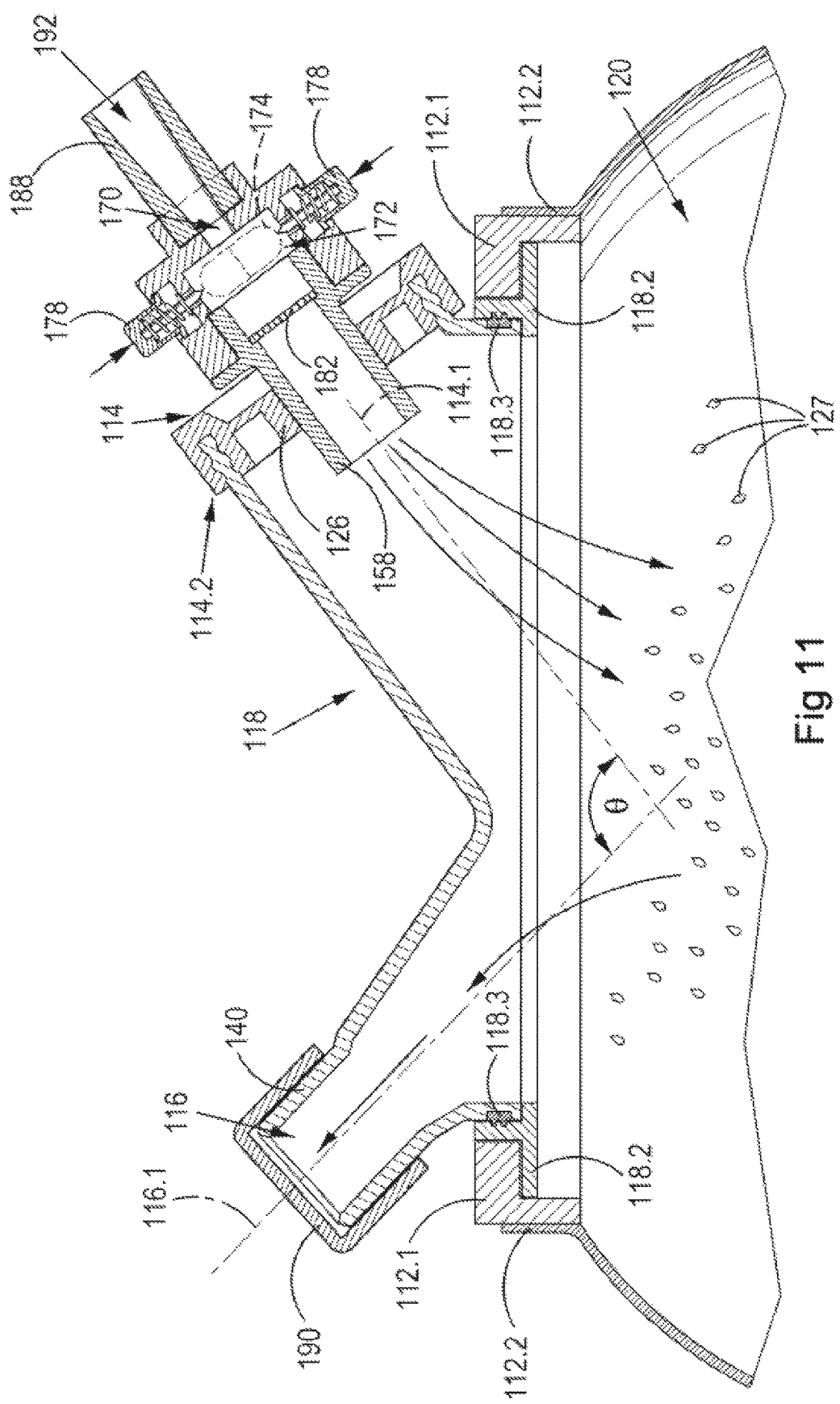
FIG. 11 shows a cross-sectional side view of another embodiment of the DPI, prior to piercing of a dry powder capsule.

As may best be seen in FIG. 4, and as mentioned hereinbefore, the body 118 has the inlet 114 and outlet 116 ports integrally formed therein, in unitary construction, such that the longitudinal axes 114.1, 116.1 of the inlet 114 and outlet 116 ports, respectively, when intersected, define an arc having an angle (shown as Θ) of between 30 degrees and 170 degrees. The V-shape defined by the inlet 114 and outlet 116 ports has a general angle of 90 degrees which corresponds generally to angle (Θ) which is similarly approximately 90 degrees in the embodiment shown in FIGS. 11 to 19. As shown in FIGS. 4, 10, and 11, this assists in ensuring that the inhalant drug (shown as microdispersion droplets or powder particles 127) fully enters the chamber 120 first rather than being passed directly through between inlet 114 and outlet 116 as would have been the case if they had been in register, i.e. when the angle would have been 180 degrees or thereabouts, thereby facilitating dispersion or vaporisation of the powder particles 127.

In this way, the propelled particles 127 enter the chamber 120 in a smooth fluid flow manner without impacting, and thereby being retained, either on internal structures to any great extent, nor being expelled at speed directly into the oral cavity or throat of the user by shooting directly through outlet 116. The chamber 120 thus serves as reservoir for the inhalant drug and facilitates particle cloud formation or dispersion within the chamber 120, from where the inhalant particles 127 can be inhaled at a slow flow rate—something no other DPI inhaler can offer as far as the Applicant is aware. The angle of the inlet 114 and outlet 116, and the fact that they are both valve-less, both therefore provide smooth, unimpeded entry and exit of the inhalant particles 127 into and out of the chamber 120. This adds to the fact that a much higher percentage of the active drug is then inhaled by a user through outlet 116 than would have been the case without such an arrangement.

Furthermore, the provision of the bag 112 on the operative underside of the body 118 ensures that the bag 112 does not impede visual referencing of the DPI device 156 by the user during use (see FIG. 5), leading also to more accurate, yet less conspicuous, use of the device 110 by the user.

Figure 3A:
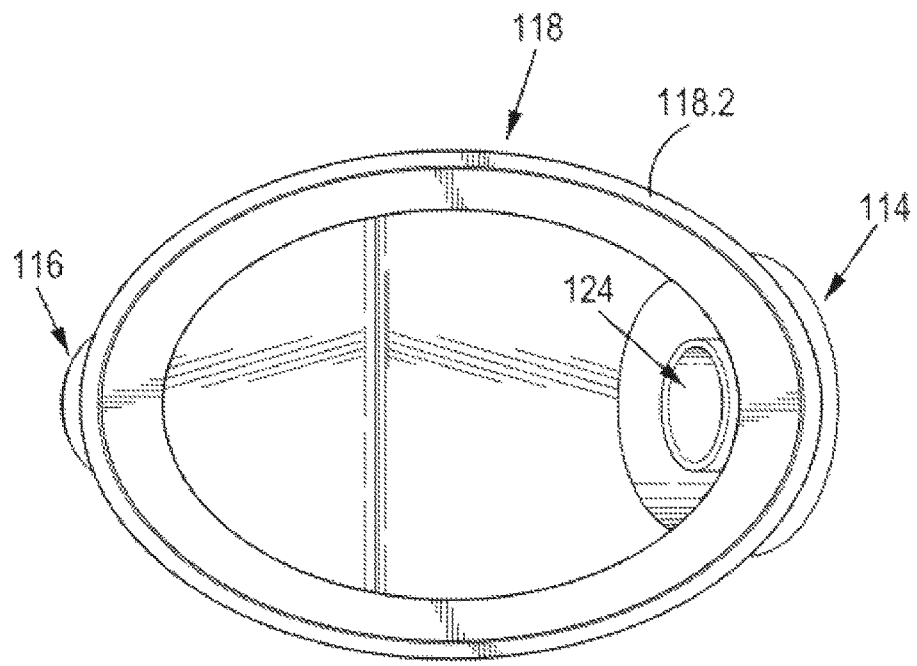
FIGS. 3A & 3B are bottom plan views of the V-shaped body of the spacer device of the invention, with the version shown in FIG. 3B including a cross-hair filament extending across an inner cavity of the spacer body.
Figure 3B:
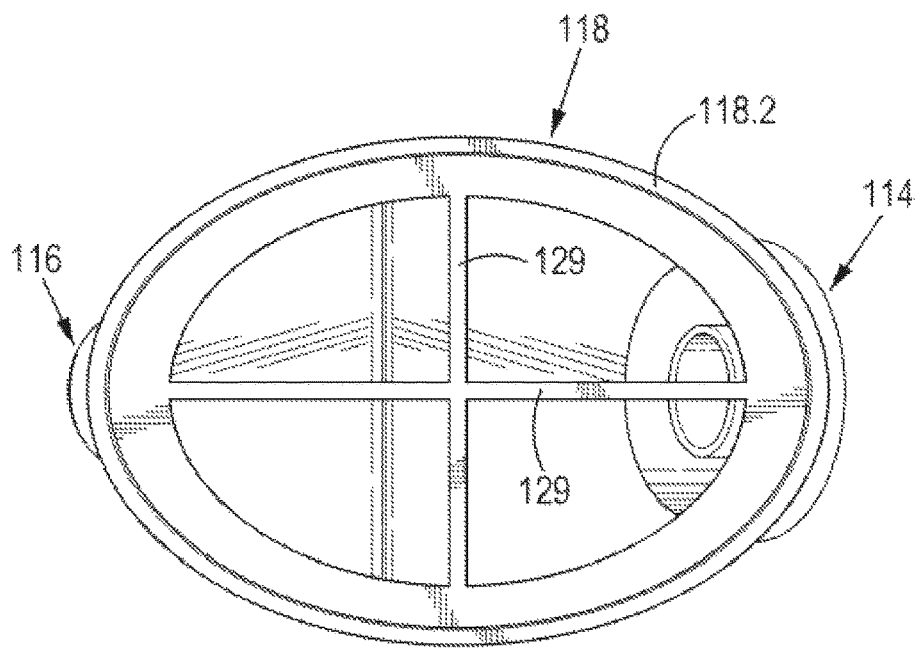
Figure 6A:
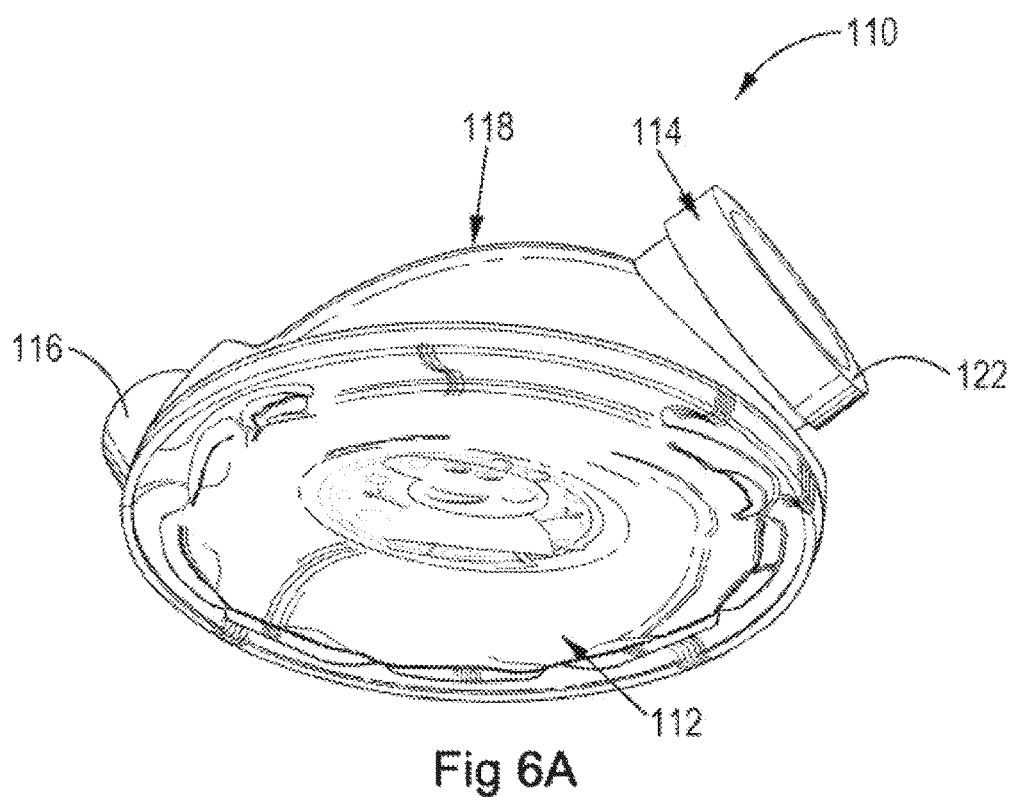
FIGS. 6A and 6B show the bag folded into the inner cavity defined by the body, to aid portability.
Figure 6B:
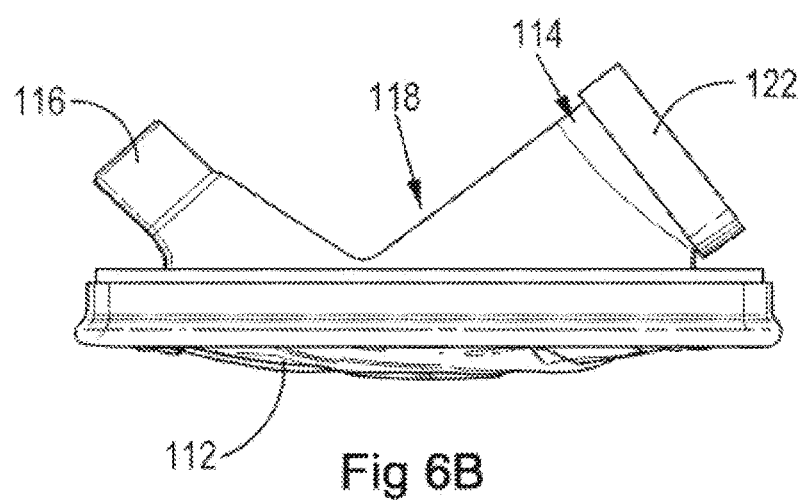

As may be seen in FIGS. 3A and 3B, as well as in profile in FIGS. 4, 10 and 11, the interior of the body 118 is V-shaped, commensurate with the outside of the body 118. The interior of the body 118 includes, in one embodiment, shown in FIGS. 3B and 8, a cross-hair filament 129 that prevents the bag 112 from being sucked completely into the interior of the body 110, potentially blocking inlet 114 and outlet 116. However, testing has shown that the possibility of this occurring is extremely low, if non-existent, and in the other embodiments shown the filament structure is omitted. FIGS. 6A and 6B show the inhaler spacer device 110 of the invention in which the bag 112 is nearly completely received or folded within the interior of the body 118 for portability or transportation purposes. This serves to decrease the size and conspicuousness of the device 110, making it easy to fit the device 110 into a purse, handbag, or carry bag.

Figure 7:
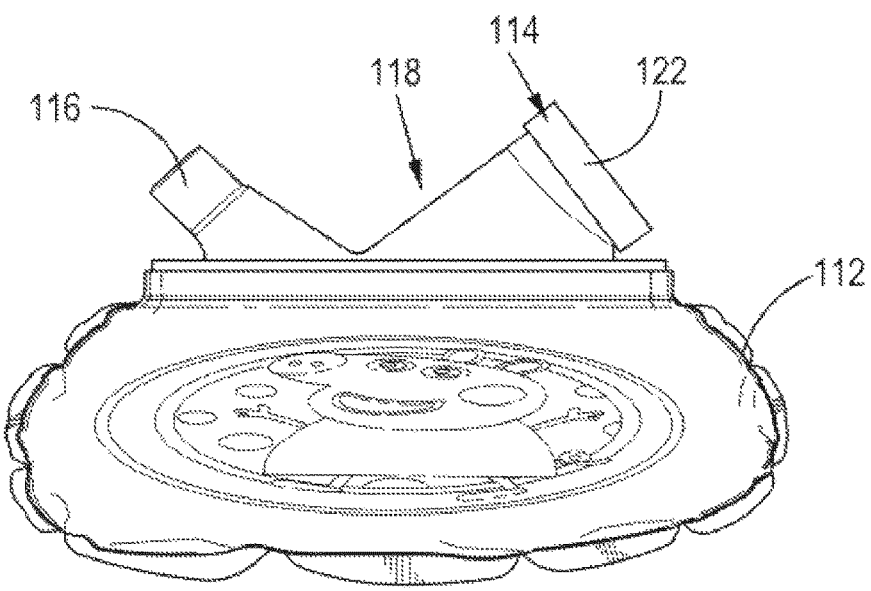
FIG. 7 shows a bag slightly decreasing in vertical cross-section due to inhalation.
Figure 8:
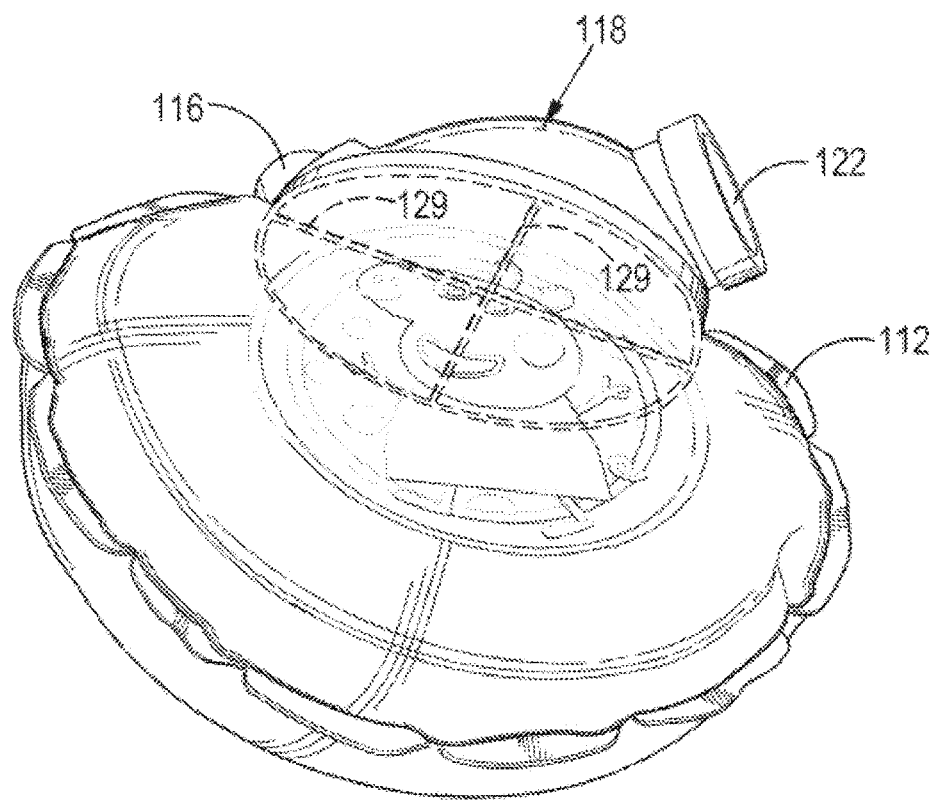
FIG. 8 shows a part cross-sectional lower 3-D view of a spacer device in accordance with one aspect of the invention.

As may be seen in FIG. 7, during inhalation, the bag 112 decreases in size, during use, only slightly in vertical cross-section, generally maintaining its vertical dimensions due to the resilience of seam 112.3 forming part of the bag 112. Inhalation thus generally results preferentially in the two opposing sides or "cheeks" 112.4, 112.5 (best seen in FIG. 1) of the bag 112 being drawn closer to each other, rather than the bag 112 being sucked into, and collapsing inwardly into the inner cavity of the body 110. The Applicant has found that even during sharp inhalation, not only the configuration and shape of the bag 112, (especially the resiliently flexible, shape-memory seam 112.3), but also the fact that the increase in negative pressure may reach a level where air is then entrained through the DPI attached to the mouthpiece and flows through the interior/cavity of the base of the present spacer device, collectively prevent the bag 112 from being sucked into the inner cavity defined by the housing 110 and potentially occluding the outlet 116.

Advantageously, a smaller bag can be used for children, the elderly, or those with compromised lung function (or to avoid conspicuousness), while larger bags may be used for adults.

The longitudinal axis (major axis) of the oval perimeter 118.1 of the spacer device 118 in this embodiment is 9 cm. In another embodiment, this may be less (down to 2 cm, or less), or more (up to 20 cm, or more). The axis defining the maximum width (minor axis) of the oval perimeter 118.1 in this embodiment is 6.5 cm. In another embodiment, this may be less (down to 1 cm, or less) or more (up to 15 cm, or more). The ratio between the major axis and minor axis is typically 1.38:1.

The thickness of the wall of the V-shaped mounting can be adjusted for considerations relating to weight, strength, feel, and construction. In this embodiment, the wall is 2 mm thick through most of the mounting although this may vary. In other embodiments, this may be less, (down to 1 mm, or less) or more (up to 8 mm, or more).

Usefully, the body (or "base") 118 and the bag 112—together defining chamber 120—can be separable allowing the bag 112 to be disconnected from the body 112. Amongst other indications, this disconnection may be indicated when a bag 112 is required to be cleaned or replaced when worn or contaminated, or simply replaced with one of a different size (volume) bag 112 depending on the need and capabilities of the patient.

As may best be seen in FIG. 9, the bag 112, when ready for use, spontaneously adopts a fully inflated position filled with air. The bag 112 is typically made of pliable and thin material providing negligible resistance to expansion and collapse making it capable of full deflation and re-inflation while the patient inhales and exhales during rebreathing. As mentioned hereinbefore, the bag 112 is metallised (typically made from a thin-section, easily collapsible polymeric metallised film such as Mylar®) such that it conducts electricity and therefore does not develop static electricity. The material thickness in one embodiment is 12.5 microns but is thinner (down to 5 microns or less) in another embodiment, or in a further embodiment, thicker (up to 25 microns, or more).

The bag 112 can either collapse fully during inhalation allowing complete emptying of all the medication particles 127 originally expelled into the chamber 120 from the DPI in a single breath, or collapse partially (depending on the patient's breathing comfort and capabilities) whereupon the user can re-breath by exhaling back into the bag before re-inhaling, allowing emptying to take place over a few breaths. The bag 120 can either re-expand fully or partially during exhalation to accommodate any unabsorbed medication 127. If during a deep exhalation the chamber 120 fills, the valve-less inlet 114 will allow the excess air to escape through the DPI holder 156 (if necessary) thus avoiding any pressure build-up within the spacer device 110. Similarly, if the patient continues with a deep inhalation after the chamber 120 has emptied and collapsed completely, the casing around the DPI 156 (at least the embodiment shown in FIGS. 1 to 5, will allow additional air to be entrained into the spacer device 110 and pass through the body 118 to the patient thus avoiding any limitation to inspiration.

The invention extends also to different forms of a DPI. Three embodiments of the DPI are shown generally by reference numerals 158, 258, ad 358 in FIGS. 1-5, 10, and 11-12, respectively. Generally, the DPI of the invention includes a body having an inlet and outlet, the inlet and outlet being in fluid flow communication with a chamber defined within the DPI body, the chamber being shaped and dimensioned to receive a powdered inhalant drug.

In the embodiment shown in FIGS. 1 to 5, the DPI 156 includes body 156.1. The body includes outlet 158 that is connected to the inlet 116 of the spacer device 110. The body further includes canister 160 that serves as expulsion or propellant means. The canister contains a propellant (not shown) that is in fluid flow connection with inlet 162 via conduit 164, passing through collar 166 and through inlet 170 into the interior of chamber 172 shaped and dimensioned to receive and hold a capsule 174, or any other dispenser containing dry powder to be inhaled.

The inlet 170 is in the form of an aperture defined in a rear wall of the DPI chamber 172 that snugly fits around the conduit 164 entering the chamber 172.

Prior to activation of the propellant, the capsule 174 is pierced using piercing means in the form of diametrically opposed pins 176 by way of the user pushing buttons 178 inwardly, forcing pins 176 into the interior of the chamber 174. The pins penetrate an outer encapsulation layer of the capsule 174 allowing the drug contents thereof to be spilled into the chamber 172. The buttons and pins are spring-loaded by way of coil springs 180, so that they are biased outwardly, out of the interior of the chamber 174.

When actuated by pushing, the propellant passes from the canister 160, through conduit 164 and inlet 170 into the interior of the chamber 172, where it expels the liberated dry powder drug through outlet 158. A filter 182 is interposed between the chamber 172 and the outlet 158 to prevent lumps or oversize particles of the drug from leaving the chamber 172 and entering spacer device 110 chamber 120.

In another embodiment, shown in FIG. 10, the expulsion means is in the form of a conduit 164 connected to a positive pressure pump, such as a nebuliser or oxygen supply 184, the conduit 164 passing through connector 186 through inlet 170 into the interior of chamber 172. In this embodiment, the capsule is pierced as before, following which the pressure pump is activated to thereby expel the dry powder drug from the chamber 172, through filter 182, through outlet 158, into the chamber 120 of the spacer device 110.

In a still further embodiment of the DPI, the expulsion means is in the form of an entrainment mouthpiece 188 shaped and dimensioned to allow a user of the DPI 156 device to expel the contents of the DPI chamber 172 through the outlet 158 by forced expiration. When use is made of the entrainment mouthpiece 188, the opposed outlet 116 of the spacer device 110 is closed using a removable cap 190 that occludes the outlet 116 of the spacer device. As such, the outlet cap fits snugly over the outlet 116 of the spacer device 110. In use, a user will attach the DPI 156 of this embodiment to an inlet 114 of the spacer device 110, attach the cap 190 (or, alternatively, close outlet 116 using their hand), pierce the capsule 174 to liberate the drug powder, and then blow or exhale forcefully into entrainment mouthpiece 188 via inlet 192 defined by the mouthpiece 188, thereby to expel the powdered drug from the DPI chamber 172, through the DPI outlet 158, through the spacer device inlet 114, into the spacer device chamber 120 formed by the spacer device body 118 and the bag 120 associated therewith, from where the vaporised drug particles (in microdispersion form) can be inhaled with regular tidal breathing and/or rebreathing out of spacer device outlet 116, once the cap has been removed.

Similarly, as described above, the skilled addressee will appreciate that the expulsion means may comprise any suitable form of air compressor configured to expel the dry powder medication into the chamber 172, such as a syringe, a compressible bulb, or the like.

The Applicant has identified the following advantages of the invention:

The low resistance to flow and easy collapsibility of the bag 112 provides ease-of-use to patients;

This is the first and only DPI device, as far as the Applicant is aware, that allows the user to control inhalation flow rates with no necessity for timing and co-ordination;

Allows rebreathing if user not capable of a single breath manoeuvre; and

If patient is not capable, there is still the capacity to not change flow rate or pattern of breathing (such as, shallow or deep) or change the volume of the chamber.

Furthermore, the Applicant has identified the following advantages associated with the invention. The metallic nature of the body 118 and bag 112 removes the potential for static electricity to cause particles to adhere to the interior walls and be retained in the spacer device 110. The bag 112 is detachable and comes in different volumes depending on medical need at the time and patient preference. The bag 112 is extremely pliant with extremely low resistance to inflation to full volume and deflation to empty or near-empty. The body 118 has an entrance end to which the DPI is connected and through which drug is expelled directly into the bag when the DPI is actuated. The angle of the entrance ensures that, following actuation of the DPI, the plume of the medication fans directly and in generally straight lines into the volume of the bag where the micro-dispersed particles come to rest largely by their own inertia, thereby forming a reservoir cloud of particles suspended in air and ready for inhalation.

In addition to the angle, the entrance being valveless (i.e. unvalved) ensures the particles contained in the spreading plume minimises impaction and retention against solid walls and surfaces, a function not only of the entrance angles, but also dependent on the size of the bag.

During inhalation, the angle of the exit end (mouthpiece) and the absence of valves promotes unimpeded and laminar flow of the drug particles directly from the reservoir cloud in the bag through the mouthpiece into the mouth and then into the airway. The reservoir nature of the particles in the chamber (bag) allows the patient, when well and capable, to choose the desired flow rate and breath pattern for optimal lung deposition—ideally slow flow rate and deep inspiration. On the other hand, if the patient is unwell and unable to empty the chamber (bag) or adjust the breathing pattern, the valve-less closed-circuit nature of the system will allow rebreathing which, over a few breaths, will empty any remaining drug from the chamber 120 by washout. During the exhalation phase of rebreathing, the angle of the outlet 116 once again favours unimpeded flow of exhaled air and any unabsorbed medication back into the volume of the bag, re-inflating the bag and re-forming the reservoir cloud that is then available for re-inhalation into the lung again. It is important to note that various types of extraneous mouthpieces (not shown) can be added to the outlet 116 depending on patient or condition requirements. This would include a face mask, if required.

The inferior positioning of the collapsible chamber 120 allows for a larger space (volume) to be used without significantly increasing intrusiveness to the patient. Larger volumes in chamber 120 are generally more efficient in drug delivery allowing better dispersal of drug particle droplets 127 and less inclination for impaction of drug particle droplets 127 on side walls. Current spacers of which the Applicant is aware have no flexibility regarding changing the volume of the spacer and essentially there are only two sizes of spacer chamber—small and large. The current invention offers easier emptying of larger volumes during single deep inhalation (low resistance to flow, no valve at outlet 116, collapsing bag 120 promoting emptying), and if emptying is not achievable in a single inhalation, then rebreathing will achieve this by washout with the valve-less, closed-circuit environment—usually within three to five breaths. If still not achievable, then switching to a smaller bag is a readily available option.

Essentially, the total amount of drug emitted from the DPI into the bag 112 is captured within the spacer device and made available for unimpeded inhalation into the lungs either with single breath or rebreathing, and with losses minimised at every step along the way. In addition, during use, the amount of bag movement is an important indicator as to the amount of medication being inhaled. This provides accurate and important feedback and reassurance to the patient and/or observer and has been shown to be critical in promoting optimal use and adherence with treatment. No co-ordination or timing of inhalation in relation to actuation is required. Critically, the current invention provides the user full control over flow rate at all times, and very low flow rates can be generated without compromising medication delivery—either using a single deep breath or multiple breaths such as during a simple tidal re-breathing manoeuvre. Low flow rates have been shown to minimize the amount of drug impacting and being retained in the mouth, pharynx and glottic area, while at the same time, ensuring that inhalant drug particles entering the airway are deposited more evenly through the lung, delivered to more peripheral parts of the lung, and penetrate better into diseased areas where they are needed most.

As mentioned before, this is the first and only device of which the Applicant is aware, that allows slow deep inhalation of dry powder particles, a critical factor identified by the International Society of Aerosolised Medicine for improving: (i) the amount of medication delivered to the airways; (ii) even distribution of medication throughout the lung; (iii) more peripheral distribution of medication in the airways, and, most importantly, (iv) improved penetration of drug to diseased areas of lung where it is need most.

The device of the invention, when compared to other inhalation devices, demonstrates:

Improved efficiency of drug delivery to the airways;

Static electricity as wall particle impaction leading to drug being retained in the device not being a significant issue;

Reduced need for co-ordination between actuation and breathing;

Improved ease of use, greater comfort and portability;

Valuable visual and physiological feedback and reassurance to the patient regarding performance during the manoeuvre; and Simplicity and low cost.

In addition, all these benefits are amplified in situations where achieving efficient drug delivery is usually most difficult, such as in very young or old patients, patients who are very ill (such as during a severe asthma attack), or in patients with chronic lung disease and damaged airways.

In final summary, the invention herein described utilizes the concept of an unvalved, low resistance, closed-circuit, rebreathing, anti-static, collapsible chamber to produce an arrangement which allows a relaxed normal or low flow rate during inhalation and exhalation which is not dependent on co-ordination or any specific breathing pattern. These features are particularly beneficial when compared to current devices that the inventor is aware of, particularly when it comes to improved delivery efficiency, simplicity of use, and versatility.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

For, example the frame 50 can be integrally formed with the body 18 of the bag 12, whereby the rods are able to flex outwardly during inflation of the bag 12 but are not able to flex fully inwardly. Also, as shown in FIG. 7, the body 18 can be provided with numerous internal knobs or bulges 62 that are arranged to prevent the full collapsing of the bag 12.

In summary, Applicant believes that the present invention represents a major innovative advance in dry powder inhalation technology, wherein the user is able to inhale a cloud or vapour of well-dispersed, diluted, dry powder particles, with a slow deep inhalation, and/or regular tidal breathing and/or rebreathing or whatever breathing pattern he/she chooses. In addition, the invention provides dry powdered drug inhalation at flow rates low enough to comply with the recommendations of the ISAM report, namely 10-15 L/min—around tidal flows. As mentioned, benefits may include:

The low flows will dramatically reduce impaction in the throat and elsewhere;

This in turn will increase the number of particles (dose) delivered to the lung;

This in turn will reduce throat complications resulting from impaction and retention;

The impact on the vocal cords will be significantly less, reducing the incidence of cough;

Low flows lead to improved peripheral airway deposition, more even lung distribution, and penetration of particles to diseased ad damaged areas of lung where they are needed most;

Low flows will maximise the distribution advantages of smaller particles (nanoparticles);

Increased dispersibility in the volume of the chamber will reduce particle crowding, collision and re-aggregation which in the end, means an increase in the fine particle fraction delivered to the airways;

The particle dilution and the inhalation of the dose over a longer period of time will reduce the problems associated with delivery of dense particle formulations which are poorly tolerated, often need to be engineered to larger MMADs to improve tolerability and other delivery problems, and which in turn means they need more capsules per dose—all disadvantageous to the user; and No need for co-ordination or specific breathing patterns will improve ease-of-use and user-friendliness for all users—particularly those who need it most such as the very old, very young and very ill.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth. In the example embodiments, well-known processes, well-known device structures, and well-known technologies are not described in detail, as such will be readily understood by the skilled addressee.

The use of the terms "a", "an", "said", "the", and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. As used herein, the term "and/or" includes any and all combinations of one or more of the associated listed items. No language in the specification should be construed as indicating any non-claimed subject matter as essential to the practice of the claimed subject matter.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It is to be appreciated that reference to "one example" or "an example" of the invention, or similar exemplary language (e.g., "such as") herein, is not made in an exclusive sense. Various substantially and specifically practical and useful exemplary embodiments of the claimed subject matter are described herein, textually and/or graphically, for carrying out the claimed subject matter.

Accordingly, one example may exemplify certain aspects of the invention, whilst other aspects are exemplified in a different example. These examples are intended to assist the skilled person in performing the invention and are not intended to limit the overall scope of the invention in any way unless the context clearly indicates otherwise. Variations (e.g. modifications and/or enhancements) of one or more embodiments described herein might become apparent to those of ordinary skill in the art upon reading this application. The inventor(s) expects skilled artisans to employ such variations as appropriate, and the inventor(s)

intends for the claimed subject matter to be practiced other than as specifically described herein.

Any method steps, processes, and operations described herein are not to be construed as necessarily requiring their performance in the particular order discussed or illustrated, unless specifically identified as an order of performance. It is also to be understood that additional or alternative steps may be employed.

The invention claimed is:

1. A Dry Powder Inhaler (DPI) arrangement comprising a DPI arranged in fluid communication with a spacer device, the spacer device comprising:

a body in the form of a generally V-shaped mounting formed by an inlet passage and an outlet passage that are opposed to one another and intersect at an angle of between 30 and 170 degrees along their respective longitudinal axes; and a demountable, flexible bag attached below the body, the bag and body together defining a chamber, such that the inlet and outlet passages are in fluid flow communication with an interior of the chamber;

wherein an inlet connected to the inlet passage is configured for operative connection to the DPI containing a drug to be inhaled;

wherein an outlet connected to the outlet passage is configured to be operatively received by a user's mouth;

wherein the V-shaped mounting includes a V-shaped interior surface, and has a lower perimeter formed by merging of inferior and lateral aspects of the merging inlet passage and outlet passage, said perimeter being generally oval in shape;

wherein the DPI includes expulsion means for expelling a powdered drug from the DPI into the spacer device, said drug encapsulated in the form of a capsule, caplet, or gel covering, said expulsion means including piercing means for piercing said capsule, caplet or gel covering to liberate the powder prior to expulsion from the DPI; and wherein the flexible bag serves as reservoir to allow for the formation therewithin of a particle cloud of the drug to be inhaled following activation of the DPI, the flexible bag being configured to be at least partially inflatable and at least partially deflatable commensurate with breathing and/or rebreathing of said user.

2. The DPI arrangement of claim 1, which is valveless.

3. The DPI arrangement of claim 1, wherein the body, inlet passage, outlet passage and/or bag is configured to reduce a static electricity charge by being made of electrically conductive material.

4. The DPI arrangement of claim 3, wherein the bag is made of a metallised polymer film or aluminium foil.

5. The DPI arrangement of claim 1, wherein the body, inlet passage, outlet passage and/or bag is configured to reduce a static electricity charge by being treated with an anti-static agent.

6. The DPI arrangement of claim 1, wherein the inlet comprises a mount defining the inlet for sealingly engaging with an outlet of the DPI, the inlet surrounded by a sealing collar configured to seal against the DPI.

7. The DPI arrangement of claim 1, wherein the outlet comprises a mouthpiece defining the outlet which provides unimpeded air and drug flow between the chamber and the ambient environment or, during use, the user's mouth.

8. The DPI arrangement of claim 1, wherein the bag has an opening including a collar that is shaped and dimensioned to fit securely to a lower perimeter of the body of the spacer device to facilitate releasable attachment of the bag to the body, the collar extending along an upper periphery of the bag opening and extending at least partially around the opening of the bag.

9. The DPI arrangement of claim 8, wherein the bag opening is biased towards an open, distended position by way of being made of a resiliently flexible material.

10. The DPI arrangement of claim 8, wherein the bag is configured to spontaneously adopt a shape of an open inflated/distended position through shape or material memory, the bag being made of a pliable and thin material to permit full collapse of the bag during inhalation.

11. The DPI arrangement of claim 8, wherein the bag is provided with a peripherally extending, resiliently flexible seam which serves to resist vertical collapse of the bag during inhalation and exhalation.

12. The DPI arrangement of claim 8, wherein said bag is configured with a size, shape and/or distensibility that corresponds to a lung volume and inhalation capacity and/or capabilities of the user, the medical needs at the time of use, and/or the user preference.

13. The DPI arrangement of claim 1, wherein the outlet passage includes a filter associated therewith to prevent lumps or oversized drug particles from being expelled from the chamber or outlet.

14. The DPI arrangement of claim 1, wherein the expulsion means is in the form of a propellant canister, an outlet of which is attached in fluid flow communication with the inlet passage.

15. The DPI arrangement of claim 1, wherein the expulsion means is in the form of a conduit connected to a positive pressure gas pump or supply.

16. The DPI arrangement of claim 1, wherein the expulsion means is in the form of an entrainment mouthpiece shaped and dimensioned to allow a user of the device to expel the contents of the DPI through the inlet passage and into the chamber by exhalation.

* * * * *